(12) United States Patent
Dusch

(10) Patent No.: US 7,553,645 B2
(45) Date of Patent: Jun. 30, 2009

(54) PROCESS FOR PREPARING L-AMINO ACIDS USING IMPROVED STRAINS OF THE ENTEROBACTERIACEAE FAMILY

(75) Inventor: Nicole Dusch, Werther (DE)

(73) Assignee: Evonik Degussa GmbH, Essen (DE)

( * ) Notice: Subject to any disclaimer, the term of this patent is extended or adjusted under 35 U.S.C. 154(b) by 221 days.

(21) Appl. No.: 11/415,302

(22) Filed: May 2, 2006

(65) Prior Publication Data

US 2006/0286644 A1    Dec. 21, 2006

(30) Foreign Application Priority Data

May 3, 2005    (DE)    ................. 10 2005 020 537

(51) Int. Cl.
*C12P 13/04*    (2006.01)
*C12N 1/20*    (2006.01)

(52) U.S. Cl. .................................... 435/106; 435/252.3

(58) Field of Classification Search ................. 435/106, 435/252.33, 488, 252.3
See application file for complete search history.

(56) References Cited

U.S. PATENT DOCUMENTS 4,278,765 A    7/1981    Dababov et al.

7,041,814 B1 *    5/2006    Weinstock et al. ......... 536/24.1

FOREIGN PATENT DOCUMENTS

| WO | WO 03/008605 A2 | 1/2003 |
|---|---|---|
| WO | WO 03/008606 A2 | 1/2003 |

OTHER PUBLICATIONS

Sequence search alignment between SEQ ID No. 1 & Accession No. AEG65425.*
Sequence search alignment between SEQ ID No. 2 & Accession No. AEG65424.*
Wick, et al., "Short- and long-term changes in proteome composition and kinetic properties in a culture of *Escherichia coli* during transition from glucose-excess to glucose-limited growth conditions in continuous culture and *vice versa*" Environ. Microbiol. 3(9):588-599 (Sep. 2001).
Raman, et al., "Proteome Analysis to Assess Physiological Changes in *Escherichia coli* Grown Under Glucose-Limited Fed-Batch Conditions," Biotech. Bioeng. 92(3):384-392 (Nov. 2005).
European Search Report for EP 06112403.

* cited by examiner

*Primary Examiner*—Tekchand Saidha
(74) *Attorney, Agent, or Firm*—Michael A. Sanzo; Law Office of Michael A. Sanzo, LLC

(57) ABSTRACT

The invention relates to a process for preparing L-amino acids by fermenting recombinant microorganisms of the Enterobacteriaceae family in which the ytfQ-ORF is overexpressed.

19 Claims, 1 Drawing Sheet

SEQUENCE LISTING

<160> NUMBER OF SEQ ID NOS: 8

<210> SEQ ID NO 1
<211> LENGTH: 957
<212> TYPE: DNA
<213> ORGANISM: Escherichia coli
<220> FEATURE:
<221> NAME/KEY: CDS
<222> LOCATION: (1)..(957)
<223> OTHER INFORMATION: ytfQ coding region

<400> SEQUENCE: 1

```
atg tgg aaa cgc tta ctt ata gtc tct gca gtc tcg gca gcc atg tcg      48
Met Trp Lys Arg Leu Leu Ile Val Ser Ala Val Ser Ala Ala Met Ser
1               5                   10                  15 tct atg gcg ttg gcc gct cca tta acc gtt gga ttt tcg cag gtc gga      96
Ser Met Ala Leu Ala Ala Pro Leu Thr Val Gly Phe Ser Gln Val Gly
                20                  25                  30 tcg gaa tca ggc tgg cgt gcc gca gaa acc aat gtg gcg aaa agt gaa     144
Ser Glu Ser Gly Trp Arg Ala Ala Glu Thr Asn Val Ala Lys Ser Glu
            35                  40                  45 gcc gaa aag cgc gga atc acg ttg aaa att gcc gat ggt cag caa aag     192
Ala Glu Lys Arg Gly Ile Thr Leu Lys Ile Ala Asp Gly Gln Gln Lys
        50                  55                  60 cag gaa aac cag att aaa gcg gta cgt tcc ttc gtt gca caa ggg gtg     240
Gln Glu Asn Gln Ile Lys Ala Val Arg Ser Phe Val Ala Gln Gly Val
65                  70                  75                  80 gat gcg atc ttt atc gct ccg gtg gtc gcg aca ggt tgg gaa ccg gta     288
Asp Ala Ile Phe Ile Ala Pro Val Val Ala Thr Gly Trp Glu Pro Val
                85                  90                  95 tta aaa gag gcg aaa gat gcc gaa atc ccg gta ttc ttg ctc gat cgt     336
Leu Lys Glu Ala Lys Asp Ala Glu Ile Pro Val Phe Leu Leu Asp Arg
            100                 105                 110 tcc att gat gtg aaa gac aaa tct ctc tat atg acc acc gtc act gcc     384
Ser Ile Asp Val Lys Asp Lys Ser Leu Tyr Met Thr Thr Val Thr Ala
        115                 120                 125 gac aac atc ctc gaa ggc aag ttg att ggt gac tgg ctg gta aaa gaa     432
Asp Asn Ile Leu Glu Gly Lys Leu Ile Gly Asp Trp Leu Val Lys Glu
130                 135                 140 gtg aat ggc aaa cca tgc aac gtg gtg gag ctg cag ggc acc gtt ggg     480
Val Asn Gly Lys Pro Cys Asn Val Val Glu Leu Gln Gly Thr Val Gly
145                 150                 155                 160 gcc agc gtc gcc att gac cgt aag aaa ggc ttt gcc gaa gcc att aag     528
Ala Ser Val Ala Ile Asp Arg Lys Lys Gly Phe Ala Glu Ala Ile Lys
                165                 170                 175 aat gcg cca aat atc aaa atc atc cgc tcg cag tca ggt gac ttc acc     576
Asn Ala Pro Asn Ile Lys Ile Ile Arg Ser Gln Ser Gly Asp Phe Thr
            180                 185                 190 cgc agt aaa ggc aaa gaa gtc atg gag agc ttt atc aaa gcg gaa aac     624
Arg Ser Lys Gly Lys Glu Val Met Glu Ser Phe Ile Lys Ala Glu Asn
        195                 200                 205
```

```
aac ggc aaa aac atc tgc atg gtt tac gcc cat aac gac gac atg gtg        672
Asn Gly Lys Asn Ile Cys Met Val Tyr Ala His Asn Asp Asp Met Val
210                 215                 220 att ggt gca att cag gca att aaa gaa gcg ggc ctg aaa ccg ggc aaa        720
Ile Gly Ala Ile Gln Ala Ile Lys Glu Ala Gly Leu Lys Pro Gly Lys
225                 230                 235                 240 gat atc ctc acg ggt tcc att gac ggt gta ccg gac atc tac aaa gcg        768
Asp Ile Leu Thr Gly Ser Ile Asp Gly Val Pro Asp Ile Tyr Lys Ala
                245                 250                 255 atg atg gat ggc gaa gcg aac gcc agt gtt gaa ctg acg ccg aat atg        816
Met Met Asp Gly Glu Ala Asn Ala Ser Val Glu Leu Thr Pro Asn Met
            260                 265                 270 gca ggt ccc gcc ttc gac gcg ctg gag aaa tac aaa aaa gac ggc acc        864
Ala Gly Pro Ala Phe Asp Ala Leu Glu Lys Tyr Lys Lys Asp Gly Thr
        275                 280                 285 atg cct gaa aag ctg acg tta acc aaa tcc acc ctt tac ctg cct gat        912
Met Pro Glu Lys Leu Thr Leu Thr Lys Ser Thr Leu Tyr Leu Pro Asp
    290                 295                 300 acc gca aaa gaa gaa tta gag aag aag aaa aat atg ggg tat tga            957
Thr Ala Lys Glu Glu Leu Glu Lys Lys Lys Asn Met Gly Tyr
305                 310                 315

<210> SEQ ID NO 2
<211> LENGTH: 318
<212> TYPE: PRT
<213> ORGANISM: Escherichia coli

<400> SEQUENCE: 2

Met Trp Lys Arg Leu Leu Ile Val Ser Ala Val Ser Ala Ala Met Ser
1               5                   10                  15

Ser Met Ala Leu Ala Ala Pro Leu Thr Val Gly Phe Ser Gln Val Gly
            20                  25                  30

Ser Glu Ser Gly Trp Arg Ala Ala Glu Thr Asn Val Ala Lys Ser Glu
        35                  40                  45

Ala Glu Lys Arg Gly Ile Thr Leu Lys Ile Ala Asp Gly Gln Gln Lys
    50                  55                  60

Gln Glu Asn Gln Ile Lys Ala Val Arg Ser Phe Val Ala Gln Gly Val
65                  70                  75                  80

Asp Ala Ile Phe Ile Ala Pro Val Val Ala Thr Gly Trp Glu Pro Val
                85                  90                  95

Leu Lys Glu Ala Lys Asp Ala Glu Ile Pro Val Phe Leu Leu Asp Arg
            100                 105                 110

Ser Ile Asp Val Lys Asp Lys Ser Leu Tyr Met Thr Thr Val Thr Ala
        115                 120                 125

Asp Asn Ile Leu Glu Gly Lys Leu Ile Gly Asp Trp Leu Val Lys Glu
    130                 135                 140

Val Asn Gly Lys Pro Cys Asn Val Val Glu Leu Gln Gly Thr Val Gly
145                 150                 155                 160

Ala Ser Val Ala Ile Asp Arg Lys Lys Gly Phe Ala Glu Ala Ile Lys
                165                 170                 175

Asn Ala Pro Asn Ile Lys Ile Ile Arg Ser Gln Ser Gly Asp Phe Thr
            180                 185                 190

Arg Ser Lys Gly Lys Glu Val Met Glu Ser Phe Ile Lys Ala Glu Asn
        195                 200                 205

Asn Gly Lys Asn Ile Cys Met Val Tyr Ala His Asn Asp Asp Met Val
    210                 215                 220

Ile Gly Ala Ile Gln Ala Ile Lys Glu Ala Gly Leu Lys Pro Gly Lys
```

```
                    225                 230                 235                 240
Asp Ile Leu Thr Gly Ser Ile Asp Gly Val Pro Asp Ile Tyr Lys Ala
                        245                 250                 255

Met Met Asp Gly Glu Ala Asn Ala Ser Val Glu Leu Thr Pro Asn Met
                260                 265                 270

Ala Gly Pro Ala Phe Asp Ala Leu Glu Lys Tyr Lys Asp Gly Thr
            275                 280                 285

Met Pro Glu Lys Leu Thr Leu Thr Lys Ser Thr Leu Tyr Leu Pro Asp
        290                 295                 300

Thr Ala Lys Glu Glu Leu Glu Lys Lys Lys Asn Met Gly Tyr
305                 310                 315

<210> SEQ ID NO 3
<211> LENGTH: 957
<212> TYPE: DNA
<213> ORGANISM: Erwinia carotovora
<220> FEATURE:
<221> NAME/KEY: CDS
<222> LOCATION: (1)..(957)
<223> OTHER INFORMATION: ytfQ coding region

<400> SEQUENCE: 3 atg tac aga cgt tta ctg gta gct gtt gct gta agc acg gca tta tgt    48
Met Tyr Arg Arg Leu Leu Val Ala Val Ala Val Ser Thr Ala Leu Cys
1               5                   10                  15 ggt gcc gta cag gca aaa ccc ttg acg gtt ggg ttt tct cag att ggt    96
Gly Ala Val Gln Ala Lys Pro Leu Thr Val Gly Phe Ser Gln Ile Gly
                20                  25                  30 tca gaa tca gga tgg cgc tct gca gag act aaa gtg tcg aag caa gaa   144
Ser Glu Ser Gly Trp Arg Ser Ala Glu Thr Lys Val Ser Lys Gln Glu
            35                  40                  45 gca gag aag cgt gga ata acg cta aaa att gct gat gct cag cag aaa   192
Ala Glu Lys Arg Gly Ile Thr Leu Lys Ile Ala Asp Ala Gln Gln Lys
        50                  55                  60 caa gag aac cag att aag gct gta cgg tca ttc atc gct cag agt gtt   240
Gln Glu Asn Gln Ile Lys Ala Val Arg Ser Phe Ile Ala Gln Ser Val
65                  70                  75                  80 gat gcc ata ttt atc gca ccg gtc gtt gct aca ggc tgg gca cca gtc   288
Asp Ala Ile Phe Ile Ala Pro Val Val Ala Thr Gly Trp Ala Pro Val
                85                  90                  95 tta cag gaa gct aaa gaa gca aaa atc ccg gta ttc ctg ctt gat aga   336
Leu Gln Glu Ala Lys Glu Ala Lys Ile Pro Val Phe Leu Leu Asp Arg
                100                 105                 110 acg att gag gtt agc gat cca tcg ctg tac acc gct gct att gcc tct   384
Thr Ile Glu Val Ser Asp Pro Ser Leu Tyr Thr Ala Ala Ile Ala Ser
            115                 120                 125 gac agt gtc tat gaa gga aaa gtg gca ggg gaa tgg ctt gtg aaa gag   432
Asp Ser Val Tyr Glu Gly Lys Val Ala Gly Glu Trp Leu Val Lys Glu
        130                 135                 140 gct gca ggt aaa ccg tgt aat gtt gtc gaa ttg cag gga acg gtt ggg   480
Ala Ala Gly Lys Pro Cys Asn Val Val Glu Leu Gln Gly Thr Val Gly
145                 150                 155                 160 gct agc gtt gcg atc aac cgc aag aaa ggg ttt gct gaa ggt ata gct   528
Ala Ser Val Ala Ile Asn Arg Lys Lys Gly Phe Ala Glu Gly Ile Ala
                165                 170                 175 tca gat cca cag ata aaa att att cga tca cag tca gga gac ttt act   576
Ser Asp Pro Gln Ile Lys Ile Ile Arg Ser Gln Ser Gly Asp Phe Thr
            180                 185                 190 cgc agt aag ggt aaa gag gtc atg gaa agc ttt att aaa gct gag cag   624
Arg Ser Lys Gly Lys Glu Val Met Glu Ser Phe Ile Lys Ala Glu Gln
```

-continued

```
                195                 200                 205
aac gga aaa aat atc tgc gcg gtt tat gca cat aat gat gat atg gct      672
Asn Gly Lys Asn Ile Cys Ala Val Tyr Ala His Asn Asp Asp Met Ala
    210                 215                 220 ata ggt gct att cag gca att aaa gag gca ggc cta aaa cct ggc tca      720
Ile Gly Ala Ile Gln Ala Ile Lys Glu Ala Gly Leu Lys Pro Gly Ser
225                 230                 235                 240 caa ata aaa gtt gtc tct att gat ggt gtt ccc gat att ttc aag gcc      768
Gln Ile Lys Val Val Ser Ile Asp Gly Val Pro Asp Ile Phe Lys Ala
            245                 250                 255 atg atg aat ggt gaa gcc aat gct acc gtt gag tta aca ccc aat atg      816
Met Met Asn Gly Glu Ala Asn Ala Thr Val Glu Leu Thr Pro Asn Met
        260                 265                 270 gct gga cct gct ttt gat gct tta tta gcg atg aag aag gac gga aaa      864
Ala Gly Pro Ala Phe Asp Ala Leu Leu Ala Met Lys Lys Asp Gly Lys
    275                 280                 285 cag cca gaa aaa ttt att cag aca gag tct cgt tta ttg ctg tcc gat      912
Gln Pro Glu Lys Phe Ile Gln Thr Glu Ser Arg Leu Leu Leu Ser Asp
290                 295                 300 acg gca aaa cag gag tat gaa acc aaa aaa gat ctt ggt tat tga          957
Thr Ala Lys Gln Glu Tyr Glu Thr Lys Lys Asp Leu Gly Tyr
305                 310                 315
```

<210> SEQ ID NO 4
<211> LENGTH: 318
<212> TYPE: PRT
<213> ORGANISM: Erwinia carotovora

<400> SEQUENCE: 4

```
Met Tyr Arg Arg Leu Leu Val Ala Val Ala Val Ser Thr Ala Leu Cys
1               5                   10                  15

Gly Ala Val Gln Ala Lys Pro Leu Thr Val Gly Phe Ser Gln Ile Gly
                20                  25                  30

Ser Glu Ser Gly Trp Arg Ser Ala Glu Thr Lys Val Ser Lys Gln Glu
            35                  40                  45

Ala Glu Lys Arg Gly Ile Thr Leu Lys Ile Ala Asp Ala Gln Gln Lys
        50                  55                  60

Gln Glu Asn Gln Ile Lys Ala Val Arg Ser Phe Ile Ala Gln Ser Val
65                  70                  75                  80

Asp Ala Ile Phe Ile Ala Pro Val Val Ala Thr Gly Trp Ala Pro Val
                85                  90                  95

Leu Gln Glu Ala Lys Glu Ala Lys Ile Pro Val Phe Leu Leu Asp Arg
            100                 105                 110

Thr Ile Glu Val Ser Asp Pro Ser Leu Tyr Thr Ala Ala Ile Ala Ser
        115                 120                 125

Asp Ser Val Tyr Glu Gly Lys Val Ala Gly Glu Trp Leu Val Lys Glu
    130                 135                 140

Ala Ala Gly Lys Pro Cys Asn Val Val Glu Leu Gln Gly Thr Val Gly
145                 150                 155                 160

Ala Ser Val Ala Ile Asn Arg Lys Gly Phe Ala Glu Gly Ile Ala
                165                 170                 175

Ser Asp Pro Gln Ile Lys Ile Ile Arg Ser Gln Ser Gly Asp Phe Thr
            180                 185                 190

Arg Ser Lys Gly Lys Glu Val Met Glu Ser Phe Ile Lys Ala Glu Gln
        195                 200                 205

Asn Gly Lys Asn Ile Cys Ala Val Tyr Ala His Asn Asp Asp Met Ala
    210                 215                 220
```

-continued

```
Ile Gly Ala Ile Gln Ala Ile Lys Glu Ala Gly Leu Lys Pro Gly Ser
225                 230                 235                 240

Gln Ile Lys Val Val Ser Ile Asp Gly Val Pro Asp Ile Phe Lys Ala
            245                 250                 255

Met Met Asn Gly Glu Ala Asn Ala Thr Val Glu Leu Thr Pro Asn Met
        260                 265                 270

Ala Gly Pro Ala Phe Asp Ala Leu Leu Ala Met Lys Lys Asp Gly Lys
    275                 280                 285

Gln Pro Glu Lys Phe Ile Gln Thr Glu Ser Arg Leu Leu Leu Ser Asp
290                 295                 300

Thr Ala Lys Gln Glu Tyr Glu Thr Lys Lys Asp Leu Gly Tyr
305                 310                 315

<210> SEQ ID NO 5
<211> LENGTH: 18
<212> TYPE: DNA
<213> ORGANISM: Artificial Sequence
<220> FEATURE:
<223> OTHER INFORMATION: Primer ytfQ-1

<400> SEQUENCE: 5
accgtagccg cattttc                                                    18

<210> SEQ ID NO 6
<211> LENGTH: 18
<212> TYPE: DNA
<213> ORGANISM: Artificial Sequence
<220> FEATURE:
<223> OTHER INFORMATION: Primer ytfQ-2

<400> SEQUENCE: 6
aatcggcatc aggcatag                                                   18

<210> SEQ ID NO 7
<211> LENGTH: 1152
<212> TYPE: DNA
<213> ORGANISM: Corynebacterium glutamicum
<220> FEATURE:
<221> NAME/KEY: CDS
<222> LOCATION: (172)..(1125)

<400> SEQUENCE: 7
accgtagccg cattttcat agtgagatga aagcgattac aaacttgtga ttaacgtttt      60
atttactttt ttgaagtgtg atgtaacgca atctgttaca taacgaattg tctatagttt    120
tttcgcgaac atcttttaac caataataac taccccgacg aggacaaccc t atg tgg    177
                                                         Met Trp
                                                           1 aaa cgc tta ctt ata gtc tct gca gtc tcg gca gcc atg tcg tct atg    225
Lys Arg Leu Leu Ile Val Ser Ala Val Ser Ala Ala Met Ser Ser Met
        5                  10                  15 gcg ttg gcc gct cca tta acc gtt gga ttt tcg cag gtc gga tcg gaa    273
Ala Leu Ala Ala Pro Leu Thr Val Gly Phe Ser Gln Val Gly Ser Glu
    20                  25                  30 tca ggc tgg cgt gcc gca gaa acc aat gtg gcg aaa agt gaa gcc gaa    321
Ser Gly Trp Arg Ala Ala Glu Thr Asn Val Ala Lys Ser Glu Ala Glu
35                  40                  45                  50 aag cgc gga atc acg ttg aaa att gcc gat ggt cag caa aag cag gaa    369
Lys Arg Gly Ile Thr Leu Lys Ile Ala Asp Gly Gln Gln Lys Gln Glu
                55                  60                  65 aac cag att aaa gcg gta cgt tcc ttc gtt gca caa ggg gtg gat gcg    417
```

```
Asn Gln Ile Lys Ala Val Arg Ser Phe Val Ala Gln Gly Val Asp Ala
            70                  75                  80 atc ttt atc gct ccg gtg gtc gcg aca ggt tgg gaa ccg gta tta aaa     465
Ile Phe Ile Ala Pro Val Val Ala Thr Gly Trp Glu Pro Val Leu Lys
            85                  90                  95 gag gcg aaa gat gcc gaa atc ccg gta ttc ttg ctc gat cgt tcc att     513
Glu Ala Lys Asp Ala Glu Ile Pro Val Phe Leu Leu Asp Arg Ser Ile
100                 105                 110 gat gtg aaa gac aaa tct ctc tat atg acc acc gtc act gcc gac aac     561
Asp Val Lys Asp Lys Ser Leu Tyr Met Thr Thr Val Thr Ala Asp Asn
115                 120                 125                 130 atc ctc gaa ggc aag ttg att ggt gac tgg ctg gta aaa gaa gtg aat     609
Ile Leu Glu Gly Lys Leu Ile Gly Asp Trp Leu Val Lys Glu Val Asn
                135                 140                 145 ggc aaa cca tgc aac gtg gtg gag ctg cag ggc acc gtt ggg gcc agc     657
Gly Lys Pro Cys Asn Val Val Glu Leu Gln Gly Thr Val Gly Ala Ser
            150                 155                 160 gtc gcc att gac cgt aag aaa ggc ttt gcc gaa gcc att aag aat gcg     705
Val Ala Ile Asp Arg Lys Lys Gly Phe Ala Glu Ala Ile Lys Asn Ala
            165                 170                 175 cca aat atc aaa atc atc cgc tcg cag tca ggt gac ttc acc cgc agt     753
Pro Asn Ile Lys Ile Ile Arg Ser Gln Ser Gly Asp Phe Thr Arg Ser
180                 185                 190 aaa ggc aaa gaa gtc atg gag agc ttt atc aaa gcg gaa aac aac ggc     801
Lys Gly Lys Glu Val Met Glu Ser Phe Ile Lys Ala Glu Asn Asn Gly
195                 200                 205                 210 aaa aac atc tgc atg gtt tac gcc cat aac gac gac atg gtg att ggt     849
Lys Asn Ile Cys Met Val Tyr Ala His Asn Asp Asp Met Val Ile Gly
                215                 220                 225 gca att cag gca att aaa gaa gcg ggc ctg aaa ccg ggc aaa gat atc     897
Ala Ile Gln Ala Ile Lys Glu Ala Gly Leu Lys Pro Gly Lys Asp Ile
            230                 235                 240 ctc acg ggt tcc att gac ggt gta ccg gac atc tac aaa gcg atg atg     945
Leu Thr Gly Ser Ile Asp Gly Val Pro Asp Ile Tyr Lys Ala Met Met
            245                 250                 255 gat ggc gaa gcg aac gcc agt gtt gaa ctg acg ccg aat atg gca ggt     993
Asp Gly Glu Ala Asn Ala Ser Val Glu Leu Thr Pro Asn Met Ala Gly
260                 265                 270 ccc gcc ttc gac gcg ctg gag aaa tac aaa aaa gac ggc acc atg cct    1041
Pro Ala Phe Asp Ala Leu Glu Lys Tyr Lys Lys Asp Gly Thr Met Pro
275                 280                 285                 290 gaa aag ctg acg tta acc aaa tcc acc ctt tac ctg cct gat acc gca    1089
Glu Lys Leu Thr Leu Thr Lys Ser Thr Leu Tyr Leu Pro Asp Thr Ala
                295                 300                 305 aaa gaa gaa tta gag aag aag aaa aat atg ggg tat tgagggttgc         1135
Lys Glu Glu Leu Glu Lys Lys Lys Asn Met Gly Tyr
            310                 315
tatgcctgat gccgatt                                                 1152

<210> SEQ ID NO 8
<211> LENGTH: 318
<212> TYPE: PRT
<213> ORGANISM: Corynebacterium glutamicum

<400> SEQUENCE: 8

Met Trp Lys Arg Leu Leu Ile Val Ser Ala Val Ser Ala Ala Met Ser
1               5                   10                  15

Ser Met Ala Leu Ala Ala Pro Leu Thr Val Gly Phe Ser Gln Val Gly
            20                  25                  30

Ser Glu Ser Gly Trp Arg Ala Ala Glu Thr Asn Val Ala Lys Ser Glu
```

-continued

```
                35                  40                  45
Ala Glu Lys Arg Gly Ile Thr Leu Lys Ile Ala Asp Gly Gln Gln Lys
     50                  55                  60

Gln Glu Asn Gln Ile Lys Ala Val Arg Ser Phe Val Ala Gln Gly Val
 65                  70                  75                  80

Asp Ala Ile Phe Ile Ala Pro Val Val Ala Thr Gly Trp Glu Pro Val
                 85                  90                  95

Leu Lys Glu Ala Lys Asp Ala Glu Ile Pro Val Phe Leu Leu Asp Arg
                100                 105                 110

Ser Ile Asp Val Lys Asp Lys Ser Leu Tyr Met Thr Thr Val Thr Ala
                115                 120                 125

Asp Asn Ile Leu Glu Gly Lys Leu Ile Gly Asp Trp Leu Val Lys Glu
    130                 135                 140

Val Asn Gly Lys Pro Cys Asn Val Val Glu Leu Gln Gly Thr Val Gly
145                 150                 155                 160

Ala Ser Val Ala Ile Asp Arg Lys Lys Gly Phe Ala Glu Ala Ile Lys
                165                 170                 175

Asn Ala Pro Asn Ile Lys Ile Ile Arg Ser Gln Ser Gly Asp Phe Thr
            180                 185                 190

Arg Ser Lys Gly Lys Glu Val Met Glu Ser Phe Ile Lys Ala Glu Asn
        195                 200                 205

Asn Gly Lys Asn Ile Cys Met Val Tyr Ala His Asn Asp Asp Met Val
    210                 215                 220

Ile Gly Ala Ile Gln Ala Ile Lys Glu Ala Gly Leu Lys Pro Gly Lys
225                 230                 235                 240

Asp Ile Leu Thr Gly Ser Ile Asp Gly Val Pro Asp Ile Tyr Lys Ala
                245                 250                 255

Met Met Asp Gly Glu Ala Asn Ala Ser Val Glu Leu Thr Pro Asn Met
                260                 265                 270

Ala Gly Pro Ala Phe Asp Ala Leu Glu Lys Tyr Lys Lys Asp Gly Thr
        275                 280                 285

Met Pro Glu Lys Leu Thr Leu Thr Lys Ser Thr Leu Tyr Leu Pro Asp
    290                 295                 300

Thr Ala Lys Glu Glu Leu Glu Lys Lys Lys Asn Met Gly Tyr
305                 310                 315
```

PROCESS FOR PREPARING L-AMINO ACIDS USING IMPROVED STRAINS OF THE ENTEROBACTERIACEAE FAMILY

CROSS REFERENCE TO RELATED APPLICATIONS

The present application claims priority to German application DE 10 2005 020 537.2, filed on May 3, 2005, the contents of which is hereby incorporated by reference.

FIELD OF THE INVENTION

This invention relates to a process for preparing L-amino acids (especially L-threonine) using recombinant microorganisms (especially strains of the Enterobacteriaceae family) in which the open reading frame (ORF) designated ytfQ is enhanced, in particular overexpressed, and to said microorganisms.

BACKGROUND OF THE INVENTION

L-Amino acids, in particular L-threonine, are used in human medicine and in the pharmaceutical industry, in the foodstuff industry and, very particularly, in animal nutrition.

It is known that L-amino acids can be prepared by fermenting Enterobacteriaceae strains, in particular *Escherichia coli* (*E. coli*) and *Serratia marcescens*. Because of the great importance, efforts are continually being made to improve the preparation methods. Methodological improvements can include measures relating to fermentation technology, such as stirring or supplying with oxygen, or the composition of the nutrient media, such as the sugar concentration during the fermentation, or the working-up to the product form, for example by means of ion exchange chromatography, or the intrinsic performance properties of the microorganism itself.

Methods of mutagenesis, selection and mutant choice are used for improving the performance properties of these microorganisms. This thereby results in strains which are resistant to antimetabolites, such as the threonine analog α-amino-β-hydroxyvaleric acid (AHV), or auxotrophic for metabolites of regulatory importance and produce L-amino acids such as L-threonine.

For a number of years now, recombinant DNA methods have also been used for improving L-amino acid-producing strains of the Enterobacteriaceae family by amplifying individual amino acid biosynthesis genes and investigating the effect on production. Compiled information on the cell biology and molecular biology of *Escherichia coli* and *Salmonella* can be found in Neidhardt (ed): *Escherichia coli* and *Salmonella*, Cellular and Molecular Biology, 2$^{nd}$ edition, ASM Press, Washington, D.C., USA, (1996).

OBJECT OF THE INVENTION

The inventors have set the object of providing novel measures for improving the fermentative preparation of L-amino acids, in particular L-threonine.

Figure 1:
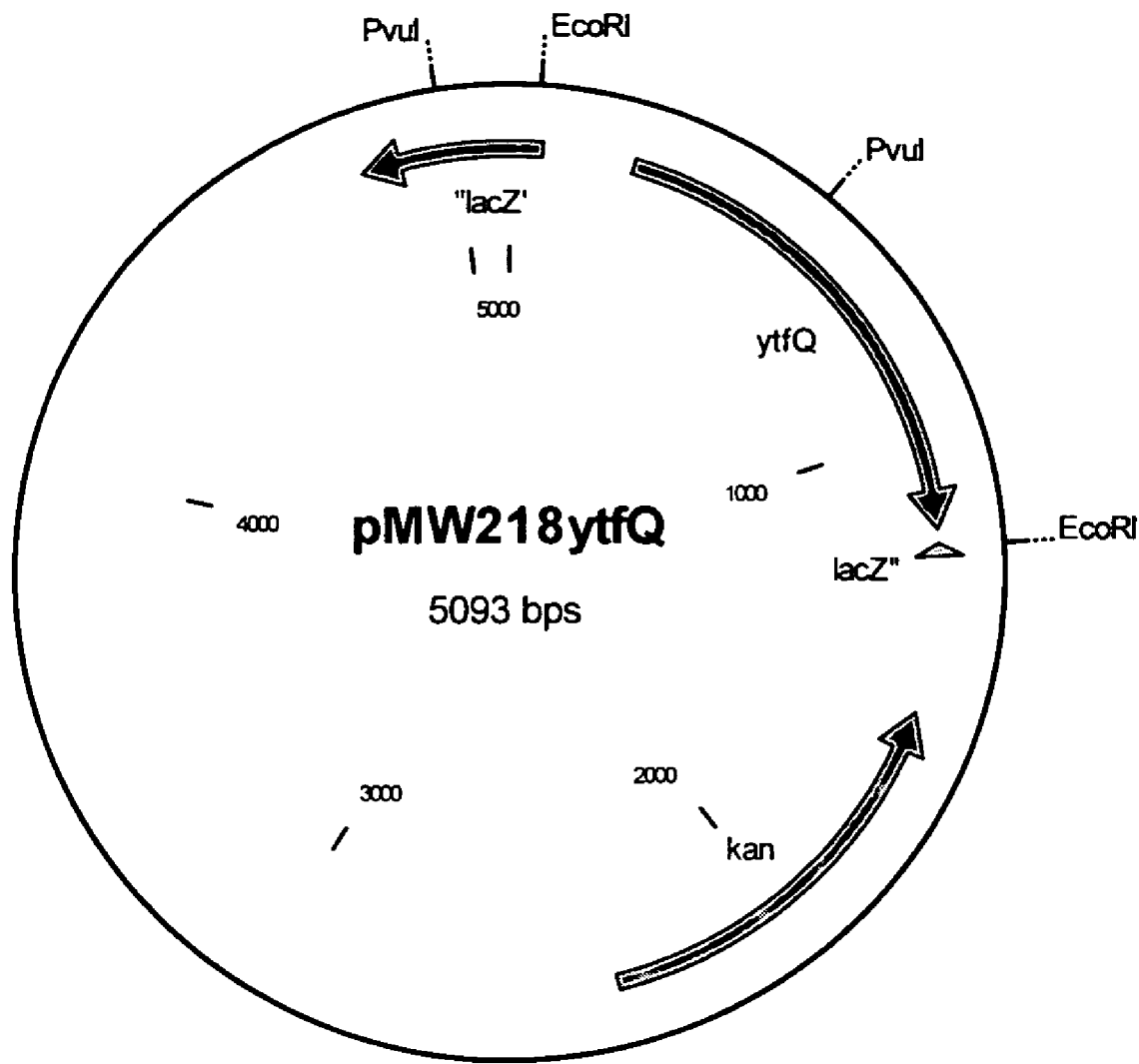
FIG. 1: Map of the ytfQ gene-containing plasmid pMW218ytfQ. Length specifications are to be regarded as being approximate. The abbreviations and designations employed have the following meanings.

kan: gene which encodes resistance to kanamycin
ytfQ: coding region of the ytfQ gene
lacZ': gene fragment which encodes the α-peptide of β-galactosidase The abbreviations for the restriction enzymes have the following meaning:
EcoRI: restriction endonuclease from *Escherichia coli*
PvuI: restriction endonuclease from *Proteus vulgaris*

DESCRIPTION OF THE INVENTION

The invention relates to recombinant microorganisms of the Enterobacteriaceae family which contain a enhanced or overexpressed open reading frame ytfQ, which encodes a polypeptide which is annotated as being a putative binding protein of an ATP-dependent sugar transporter or nucleotide sequences encoding this gene product, and which display an improved ability to form and accumulate L-amino acids, in particular L-threonine.

In each case, the microorganisms which are not recombinant for the ytfQ-ORF, which do not contain any enhanced ytfQ-ORF and on which the measures of the invention are performed, are used as the starting point for the comparison. These recombinant microorganisms include, in particular, microorganisms of the Enterobacteriaceae family in which a polynucleotide which encodes a polypeptide whose amino acid sequence is at least 80% or at least 90%, in particular at least 95%, preferably at least 98%, are at least 99%, particularly preferably 99.6% and very particularly preferably 100%, identical to an amino acid sequence selected from the group SEQ ID NO:2 and SEQ ID NO:4 is enhanced.

The microorganisms contain enhanced or overexpressed polynucleotides selected from the group:
a) a polynucleotide having a nucleotide sequence selected from SEQ ID NO:1 and SEQ ID NO:3 and the nucleotide sequences complementary thereto;
b) a polynucleotide having a nucleotide sequence which corresponds to SEQ ID NO:1 or SEQ ID NO:3 within the limits of the degeneracy of the genetic code;
c) a polynucleotide sequence having a sequence which hybridizes, under stringent conditions, with the sequence which is complementary to the sequence SEQ ID NO:1 or SEQ ID NO:3 with stringent conditions preferably being achieved by means of a washing step in which the temperature extends over a range of from 64° C. to 68° C. and the salt concentration of the buffer extends over a range of from 2×SSC to 0.1×SSC;
d) a polynucleotide having a sequence SEQ ID NO:1 or SEQ ID NO:3 which contains functionally neutral sense mutants, with the polynucleotides preferably encoding a putative binding protein of an ATP-dependent sugar transporter.

The invention also relates to a process for fermentatively preparing L-amino acids, in particular L-threonine, using recombinant microorganisms of the Enterobacteriaceae family which, in particular, already produce L-amino acids and in which at least the open reading frame (ORF) having the designation ytfQ, or nucleotide sequences encoding its gene product, is or are enhanced. Preference is given to using the microorganisms which are described.

When L-amino acids or amino acids are mentioned in that which follows, this shall mean one or more amino acids, including their salts, selected from the group L-asparagine, L-threonine, L-serine, L-glutamate, L-glycine, L-alanine, L-cysteine, L-valine, L-methionine, L-proline, L-isoleucine, L-leucine, L-tyrosine, L-phenylalanine, L-histidine, L-lysine, L-tryptophan, L-arginine and L-homoserine. L-threonine is particularly preferred.

In this connection, the term "enhancement" describes the increase, in a microorganism, of the intracellular activity or concentration of one or more enzymes or proteins which are encoded by the corresponding DNA, with, for example, the copy number of the gene or genes, or of the ORF or ORFs, being increased by at least one (1) copy, use being made of a strong promoter operatively linked to the gene or of a gene or allele or ORF which encodes a corresponding enzyme or protein having a high activity, and, where appropriate, these measures being combined.

A segment of a nucleotide sequence which encodes, or can encode, a protein and/or a polypeptide or ribonucleic acid to which the prior art is unable to assign any function is designated an open reading frame (ORF). After a function has been assigned to the nucleotide sequence segment in question, this segment is generally referred to as being a gene. Alleles are generally understood as being alternative forms of a given gene. The forms are distinguished by differences in the nucleotide sequence. In general, the protein, or the ribonucleic acid, encoded by a nucleotide sequence, i.e. an ORF, a gene or an allele, is designated a gene product.

The enhancement measures, in particular overexpression, generally increase the activity or concentration of the corresponding protein by at least 10%, 25%, 50%, 75%, 100%, 150%, 200%, 300%, 400% or 500%, maximally up to 1000% or 2000%, based on that of the wild-type protein or on the activity or concentration of the protein in the parent strain or microorganism which is not recombinant for the corresponding enzyme or protein. The non-recombinant microorganism or parent strain is understood as being the microorganism on which the measures according to the invention are performed.

The invention relates to a process for preparing L-amino acids by fermenting recombinant microorganisms of the Enterobacteriaceae family, characterized in that
  a) the desired L-amino acid-producing microorganisms, in which the open reading frame ytfQ, or nucleotide sequences or alleles encoding the gene products thereof, is/are enhanced, in particular overexpressed, are cultured in a medium under conditions under which the desired L-amino acid is accumulated in the medium or in the cells, and preferably
  b) the desired L-amino acid is isolated, with, where appropriate, the fermentation broth constituents and/or the biomass remaining in its/their entirety or in portions (from ≧0 to 100%) in the isolated product or being removed completely.

The microorganisms which have a enhanced or overexpressed open reading frame (ORF) designated ytfQ, and which are in particular recombinant, are likewise part of the subject matter of the present invention, can produce L-amino acids from glucose, sucrose, lactose, fructose, maltose, molasses, where appropriate starch and where appropriate cellulose or from glycerol and ethanol. The microorganisms are representatives of the Enterobacteriaceae family and are selected from the genera *Escherichia*, *Erwinia*, *Providencia* and *Serratia*. The genera *Escherichia* and *Serratia* are preferred. The species *Escherichia coli* may be mentioned, in particular, in the case of the genus *Escherichia* while the species *Serratia marcescens* may be mentioned, in particular, in connection with the genus *Serratia*.

In general, recombinant microorganisms are generated by means of transformation, transduction or conjugation, or a combination of these methods, with a vector which contains the desired ORF, the desired gene, an allele of this ORF or gene, or parts thereof, and/or a promoter which potentiates the expression of the ORF or gene. This promoter can be the promoter which has been produced by enhancing mutation from the endogenous regulatory sequence located upstream of the gene or ORF; alternatively, an efficient promotor has been fused to the gene or ORF.

Examples of strains of the genus *Eschericia*, in particular of the species *Escherichia coli* which produce L-threonine and which are suitable as parent strain include:

| | |
|---|---|
| *Escherichia coli* H4581 | (EP 0 301 572) |
| *Escherichia coli* KY10935 | (Bioscience Biotechnology and Biochemistry 61(11): 1877-1882 (1997) |
| *Escherichia coli* VNIIgenetica MG442 | (US-A-4278,765) |
| *Escherichia coli* VNIIgenetica M1 | (US-A-4,321,325) |
| *Escherichia coli* VNIIgenetica 472T23 | (US-A-5,631,157) |
| *Escherichia coli* BKIIM B-3996 | (US-A-5,175,107) |
| *Escherichia coli* cat 13 | (WO 98/04715) |
| *Escherichia coli* KCCM-10132 | (WO 00/09660). |

Examples of L-threonine-producing strains of the genus *Serratia*, in particular of the species *Serratia marcescens*, which are suitable as parent strain include:

*Serratia marcescens* HNr21 (Applied and Environmental Microbiology 38(6):1045-1051 (1979))

*Serratia marcescens* TLr156 (Gene 57(2-3): 151-158 (1987))

*Serratia marcescens* T-2000 (Applied Biochemistry and Biotechnology 37(3): 255-265 (1992)).

L-Threonine-producing strains of the Enterobacteriaceae family preferably possess, inter alia, one or more of the genetic or phenotypic features selected from the group: resistance to α-amino-β-hydroxyvaleric acid, resistance to thialysine, resistance to ethionine, resistance to α-methylserine, resistance to diaminosuccinic acid, resistance to α-aminobutyric acid, resistance to borrelidin, resistance to cyclopentanecarboxylic acid, resistance to rifampicin, resistance to valine analogs such as valine hydroxamate, resistance to purine analogs, such as 6-dimethylaminopurine, requirement for L-methionine, possible partial and compensatable requirement for L-isoleucine, requirement for mesodiaminopimelic acid, auxotrophy in regard to threonine-containing dipeptides, resistance to L-threonine, resistance to threonine raffinate, resistance to L-homoserine, resistance to L-lysine, resistance to L-methionine, resistance to L-glutamic acid, resistance to L-aspartate, resistance to L-leucine, resistance to L-phenylalanine, resistance to L-serine, resistance to L-cysteine, resistance to L-valine, sensitivity to fluoropyruvate, defective threonine dehydrogenase, possible ability to utilize sucrose, enhancement of the threonine operon, enhancement of homoserine dehydrogenase I-aspartate kinase I, preferably of the feedback-resistant form, enhancement of homoserine kinase, enhancement of threonine synthase, enhancement of aspartate kinase, possibly of the feedback-resistant form, enhancement of aspartate semialdehyde dehydrogenase, enhancement of phosphoenol-pyruvate carboxylase, possibly of the feedback-resistant form, enhancement of phosphoenolpyruvate synthase, enhancement of transhydrogenase, enhancement of the RhtB gene product, enhancement of the RhtC gene product, enhancement of the YfiK gene product, enhancement of a pyruvate carboxylase and attenuation of acetic acid formation.

It has been found that, following overexpression of the gene or the open reading frame (ORF) ytfQ, or its alleles, microorganisms of the Enterobacteriaceae family display an improved ability to form and accumulate L-amino acids, in particular L-threonine.

The nucleotide sequences of the *Escherichia coli* genes or open reading frames (ORFs) belong to the prior art and can be obtained from the *Escherichia coli* genome sequence published by Blattner et al. (Science 277: 1453-1462 (1997)). It is known that endogenous enzymes (methionine aminipeptidase) are able to cleave off the N-terminal amino acid methionine. The nucleotide sequence for the ytfQ-ORF from *Erwinia carotovora*, which likewise belongs to the Enterobacteriaceae family, has also been disclosed (Accession No.: NC_004547 (Region: 4740175-4739870)).

The gene product of the ytfQ-ORF of *Escherichia coli* K12 is annotated as being a putative binding protein of an ATP-dependent sugar transporter. It is furthermore described as being a periplasmic binding protein component of a putative D-ribose transport protein of the ABC transporter family, or as being a putative LACI-type regulator of transcription, or as being a precursor of the periplasmic binding protein of an ABC transporter.

The gene has been given Accession No.: U00096 (Region: 4447985-4448941), Alternative gene name: b4227 The nucleic acid sequences can be obtained from the databases belonging to the National Center for Biotechnology Information (NCBI) of the National Library of Medicine (Bethesda, Md., USA), the nucleic acid sequence database of the European Molecular Biology Laboratories (EMBL, Heidelberg, Germany or Cambridge, UK) or the Japanese DNA database (DDBJ, Mishima, Japan).

For the sake of greater clarity, the known sequence for the ytfQ-ORF of *Escherichia coli* is shown as SEQ ID NO:1 and the known sequence for the ytfQ-ORF of *Erwinia carotovora* is depicted under SEQ ID NO:3. The proteins encoded by these reading frames are depicted as SEQ ID NO:2 and SEQ ID NO:4.

The open reading frames described in the passages indicated can be used in accordance with the invention. In addition, it is possible to use alleles of the genes or open reading frames, which result from the degeneracy of the genetic code or as a consequence of functionally neutral sense mutations. Preference is given to using endogenous genes or endogenous open reading frames. "Endogenous genes" or "endogenous nucleotide sequences" are understood as being the genes or open reading frames or alleles or nucleotide sequences which are present in a species population.

The alleles of the ytfQ-ORF, which contain functionally neutral sense mutations, include, inter alia, those which lead to at most 40 or to at most 30 or to at most 20, preferably to at most 10 or to at most 5, very particularly preferably to at most 3 or to at most 2, or to at least one, conservative amino acid substitution in the protein which they encode.

In the case of the aromatic amino acids, the substitutions are said to be conservative when phenylalanine, tryptophan and tyrosine are substituted for each other. In the case of the hydrophobic amino acids, the substitutions are said to be conservative when leucine, isoleucine and valine are substituted for each other. In the case of the polar amino acids, the substitutions are said to be conservative when glutamine and asparagine are substituted for each other. In the case of the basic amino acids, the substitutions are said to be conservative when arginine, lysine and histidine are substituted for each other. In the case of the acid amino acids, the substitutions are said to be conservative when aspartic acid and glutamic acid are substituted for each other. In the case of the hydroxyl group-containing amino acids, the substitutions are said to be conservative when serine and threonine are substituted for each other.

It is also possible to use nucleotide sequences which encode variants of said proteins, which variants additionally contain an extension or truncation by at least one (1) amino acid at the N terminus or C terminus. This extension or truncation amounts to not more than 40, 30, 20, 10, 5, 3 or 2 amino acids or amino acid residues.

Suitable alleles also include those which encode proteins in which at least one (1) amino acid has been inserted or deleted. The maximum number of such changes, termed indels, can affect 2, 3, 5, 10, but in no case more than 20, amino acids.

Suitable alleles furthermore include those which can be obtained by means of hybridization, in particular under stringent conditions, using SEQ ID NO:1 or SEQ ID NO:3 or parts thereof, in particular the coding regions or the sequences which are complementary thereto. The skilled person can find instructions for identifying DNA sequences by means of hybridization in, inter alia, the manual "The DIG System Users Guide for Filter Hybridization" supplied by Boehringer Mannheim GmbH (Mannheim, Germany, 1993) and Liebl et al. (International Journal of Systematic Bacteriology 41: 255-260 (1991)). The hybridization takes place under stringent conditions, that is under conditions such that the only hybrids formed are those in which the probe and target sequence, i.e. the polynucleotides treated with the probe, are at least 70% identical. It is known that the stringency of the hybridization, including the washing steps, is influenced and/or determined by varying the buffer composition, the temperature and the salt concentration. In general, the hybridization reaction is carried out at a stringency which is relatively low as compared with that of the washing steps (Hybaid Hybridization Guide, Hybaid Limited, Teddington, UK, 1996).

For example, a buffer corresponding to 5×SSC buffer can be used for the hybridization reaction at a temperature of approx. 50° C.-68° C. Under these conditions, probes can also hybridize with polynucleotides which possess less than 70% identity with the sequence of the probe. These hybrids are less stable and are removed by washing under stringent conditions. This can be achieved, for example, by lowering the salt concentration down to 2×SSC and, where appropriate, subsequently to 0.5×SSC (The DIG System User's Guide for Filter Hybridization, Boehringer Mannheim, Mannheim, Germany, 1995) with the temperature being adjusted to approx. 50° C.-68° C., approx. 52° C.-68° C., approx. 54° C.-68° C., approx. 56° C.-68° C., approx. 58° C.-68° C., approx. 60° C.-68° C., approx. 62° C.-68° C., approx. 64° C.-68° C., approx. 66° C.-68° C. Temperature ranges of approx. 64° C.-68° C. or approx. 66° C.-68° C. are preferred. It is possible, where appropriate, to lower the salt concentration down to a concentration corresponding to 0.2×SSC or 0.1×SSC. By means of increasing the hybridization temperature stepwise, in steps of approx. 1-2° C., from 50° C. to 68° C., it is possible to isolate polynucleotide fragments which, for example, possess at least 70%, or at least 80%, or at least 90%, at least 91%, at least 92%, at least 93%, at least 94%, at least 95%, at least 96%, at least 97%, at least 98%, or at least 99%, identity with the sequence of the probe employed or with the nucleotide sequences shown in SEQ ID NO:1 or SEQ ID NO:3. Additional instructions for the hybridization can be obtained commercially in the form of what are termed kits (e.g. DIG Easy Hyb from Roche Diagnostics GmbH, Mannheim, Germany, Catalog No. 1603558).

In order to achieve enhancement, it is possible, for example, to increase the expression of the genes or open reading frames or alleles or to increase the catalytic properties of the protein. Both measures can be combined, where appropriate.

In order to achieve overexpression, the copy number of the corresponding genes or open reading frames can be increased, for example, or the promoter region and regulatory region or the ribosome binding site which is located upstream of the structural gene can be mutated. Expression cassettes which are incorporated upstream of the structural gene act in the same manner. It is also possible to increase expression during the course of the fermentative L-threonine production through inducible promoters; in addition, using promoters for gene expression which permits a different chronological gene expression can also be advantageous. At the level of the translational regulation of gene expression, it is possible to increase the frequency of initiation (binding of the ribosome to the mRNA) or the rate of elongation (elongation phase). Expression is likewise improved by means of measures for extending the lifespan of the mRNA. Furthermore, the enzyme activity is also enhanced by preventing the enzyme protein from being broken down. The ORFs, genes or gene constructs can either be present in plasmids having different copy numbers or be integrated, and amplified, in the chromosome. Alternatively, overexpression of the genes concerned can also be achieved by altering the composition of the media and the conduct of the culture.

Methods for overexpression are adequately described in the prior art, for example in Makrides et al. (Microbiological Reviews 60(3):512-538 (1996)). Using vectors increases the copy number by at least one (1) copy. The vectors used can be plasmids as described, for example, in U.S. Pat. No. 5,538,873. The vectors used can also be phages, for example phage Mu, as described in EP 0332448, or phage lambda ($\lambda$). The copy number can also be increased by incorporating an additional copy into another site in the chromosome, for example in to the att site of phage $\lambda$ (Yu and Court, Gene 223:77-81 (1998)). U.S. Pat. No. 5,939,307 reports that it was possible to increase the expression by incorporating expression cassettes or promoters, such as the tac promoter, the trp promoter, the lpp promoter, or the $P_L$ promoter or $P_R$ promoter of phage $\lambda$, upstream, for example, of the chromosomal threonine operon. In the same way, it is possible to use the phage T7 promoters, the gearbox promoters or the nar promoter. Such expression cassettes or promoters can also be used, as described in EP 0 593 792, to overexpress plasmid-bound genes. Using the lacI$^Q$ allele in turn makes it possible to control the expression of plasmid-bound genes (Glascock and Weickert, Gene 223, 221-231 (1998)). It is furthermore possible for the activity of the promoters to be increased by modifying their sequence by means of one or more nucleotide substitutions, by means of (an) insertion(s) and/or by means of (a) deletion(s). A different chronological gene expression can be achieved, for example, as described in Walker et al. (Journal of Bacteriology 181: 1269-80 (1999)), by using the growth phase-dependent fis promoter. The rate of elongation is influenced by the codon usage; gene expression can be enhanced by using codons for tRNAs which occur frequently in the parent strain.

The skilled person can find general instructions in this regard in, inter alia, Chang and Cohen (Journal of Bacteriology 134:1141-1156 (1978)), Hartley and Gregori (Gene 13:347-353 (1981)), Amann and Brosius (Gene 40:183-190 (1985)), de Broer et al. (Proceedings of the National Academy of Sciences of the United States of America 80:21-25 (1983)), LaVallie et al. (BIO/TECHNOLOGY 11:187-193 (1993)), in PCT/US97/13359, Llosa et al. (Plasmid 26:222-224 (1991)), Quandt and Klipp (Gene 80:161-169 (1989)), Hamilton et al. (Journal of Bacteriology 171:4617-4622 (1989)), Jensen and Hammer (Biotechnology and Bioengineering 58:191-195 (1998)) and known textbooks of genetics and molecular biology.

Plasmid vectors which can be replicated in Enterobacteriaceae, such as pACYC184-derived cloning vectors (Bartolomé et al.; Gene 102:75-78 (1991)), pTrc99A. (Amann et al.; Gene 69:301-315 (1988)) or pSC101 derivatives (Vocke and Bastia; Proceedings of the National Academy of Sciences USA 80(21):6557-6561 (1983)) can be used. In a process according to the invention, it is possible to use a strain which is transformed with a plasmid vector which carries at least the ytfQ-ORF, or nucleotide sequences, or alleles, which encode its gene product. The term "transformation" is understood as meaning the uptake of an isolated nucleic acid by a host (microorganism).

It is also possible to use sequence exchange (Hamilton et al.; Journal of Bacteriology 171:4617-4622 (1989)), conjugation or transduction to transfer mutations, which affect the expression of the given genes or open reading frames, into different strains.

More detailed explanations of the concepts of genetics and molecular biology can be found in known textbooks of genetics and molecular biology such as the textbook by Birge (Bacterial and Bacteriophage Genetics, 4$^{th}$ ed., Springer Verlag, New York (USA), 2000) or the textbook by Berg, Tymoczko and Stryer (Biochemistry, 5$^{th}$ ed., Freeman and Company, New York (USA), 2002) or the manual by Sambrook et al. (Molecular Cloning, A Laboratory Manual, (3-Volume Set), Cold Spring Harbor Laboratory Press, Cold Spring Harbor (USA), 2001).

Furthermore, when using strains of the Enterobacteriaceae family to produce L-amino acids, in particular L-threonine, it can be advantageous, in addition to enhancing the open reading frame ytfQ, to enhance one or more enzymes of the known threonine biosynthesis pathway or enzymes of anaplerotic metabolism or enzymes for producing reduced nicotinamide adenine dinucleotide phosphate or enzymes of glycolysis or PTS enzymes or enzymes of sulfur metabolism. Using endogenous genes is generally preferred. Thus, it is possible, for example, to simultaneously enhance, in particular overexpress, one or more of the genes selected from the group at least one gene of the thrABC operon encoding aspartate kinase, homoserine dehydrogenase, homoserine kinase and threonine synthase (U.S. Pat. No. 4,278,765), the pyruvate carboxylase-encoding *Corynebacterium glutamicum* pyc gene (WO 99/18228), the phosphoenolpyruvate synthase-encoding pps gene (Molecular and General Genetics 231(2): 332-336 (1992); WO 97/08333), the phosphoenolpyruvate carboxylase-encoding ppc gene (WO 02/064808), the pntA and pntB genes encoding the subunits of transhydrogenase (European Journal of Biochemistry 158: 647-653 (1986); WO 95/11985), the rhtC gene encoding the threonine resistance-mediating protein (EP-A-1 013 765), the threonine export carrier protein-encoding *Corynebacterium glutamicum* thrE gene (WO 01/92545), the glutamate dehydrogenase-encoding gdhA gene (Nucleic Acids Research 11: 5257-5266 (1983); Gene 23: 199-209 (1983); DE19907347), the ptsHIcrr operon ptsH gene encoding the phosphohistidine protein hexose phosphotransferase of the PTS phosphotransferase system (WO 03/004674), the ptsHIcrr operon ptsI gene encoding enzyme I of the PTS phosphotransferase system (WO 03/004674), the ptsHIcrr operon crr gene encoding the glucose-specific IIA component of the PTS phosphotransferase system (WO 03/004674), the ptsG gene encoding the glucose-specific IIBC component (WO 03/004670), the cysteine synthase A-encoding cysK gene (WO 03/006666), the cysB gene encoding the regulator of the cys regulon (WO 03/006666), the cysJIH operon cysJ gene encoding the NADPH sulfite reductase flavoprotein (WO 03/006666), the cysJIH operon cysI gene encoding the NADPH sulfite reductase hemoprotein (WO 03/006666), the adenylyl sulfate reductase-encoding cysJIH operon cysH gene (WO 03/006666), the sucABCD operon sucA gene encoding the decarboxylase subunit of 2-ketoglutarate dehydrogenase (WO 03/008614), the sucABCD operon sucB gene encoding the dihydrolipoyl-transsuccinase E2 subunit of 2-ketoglutarate dehydrogenase (WO 03/008614), the sucABCD operon sucC gene encoding the β-subunit of succinyl-CoA synthetase (WO 03/008615), the sucABCD operon sucD gene encoding the α-subunit of succinyl-CoA synthetase (WO 03/008615), the gene product of the *Escherichia coli* open reading frame (ORF) yibD (Accession Number AE000439 of the National Center for Biotechnology Information (NCBI, Bethesda, Md., USA, DE102004005836.9), the gene product of the *Escherichia coli* open reading frame (ORF) yjcG (Accession Number NC000913 (Region 4281276-4282925) of the National Center for Biotechnology Information (NCBI, Bethesda, Md., USA), the gene product of the *Escherichia coli* open reading frame (ORF) ytfR (Accession Number NC000913 (Region 4449081-4450583) of the National Center for Biotechnology Information (NCBI, Bethesda, Md., USA), which is also known under the designation ytfS-ORF, the gene product of the *Escherichia coli* open reading frame (ORF) ytfT (Accession Number NC000913 (Region 4450594-4451619) of the National Center for Biotechnology Information (NCBI, Bethesda, Md., USA), and the gene product of the *Escherichia coli* open reading frame (ORF) yjfF (Accession Number NC000913 (Region 4451630-4452601) of the National Center for Biotechnology Information (NCBI, Bethesda, Md., USA).

Furthermore, for the purpose of producing L-amino acids, in particular L-threonine, it can be advantageous, in addition to potentiating the open reading frame ytfQ, to attenuate, in particular eliminate or reduce the expression of one or more of the genes selected from the group the threonine dehydrogenase-encoding tdh gene (Journal of Bacteriology 169: 4716-4721 (1987)), the malate dehydrogenase (E.C. 1.1.1.37)-encoding mdh gene (Archives in Microbiology 149: 36-42 (1987)), the gene product of the *Escherichia coli* yjfA open reading frame (ORF) (Accession Number AAC77180 of the National Center for Biotechnology Information (NCBI, Bethesda, Md., USA), (WO 02/29080), the gene product of the *Escherichia coli* ytfP open reading frame (ORF) (Accession Number AAC77179 of the National Center for Biotechnology Information (NCBI, Bethesda, Md., USA), WO 02/29080), the pckA gene encoding the enzyme phosphoenolpyruvate carboxykinase (WO 02/29080), the pyruvate oxidase-encoding poxB gene (WO 02/36797), the dgsA gene (WO 02/081721), which is also known under the name mlc gene, encoding the DgsA regulator of the phosphotransferase system, the fruR gene (WO 02/081698), which is also known under the name cra gene, encoding the fructose repressor, the rpoS gene (WO 01/05939), which is also known under the name katF gene, encoding the sigma$^{38}$ factor, and the aspartate ammonium lyase-encoding aspA gene (WO 03/008603).

In this context, the term "attenuation" describes the reduction or abolition, in a microorganism, of the intra-cellular activity or concentration of one or more enzymes or proteins which are encoded by the corresponding DNA, by, for example, using a weaker promoter than in the parent strain or microorganism not recombinant for the corresponding enzyme or protein, or a gene or allele which encodes a corresponding enzyme or protein having a lower activity, or inactivating the corresponding enzyme or protein, or the open reading frame or gene, and, where appropriate, combining these measures.

In general, the attenuation measures lower the activity or concentration of the corresponding protein down to from 0 to 75%, from 0 to 50%, from 0 to 25%, from 0 to 10% or from 0 to 5% of the activity or concentration of the wild-type protein or of the activity or concentration of the protein for the parent strain or microorganism which is not recombinant for the corresponding enzyme or protein. The parent strain or microorganism which is not recombinant is understood as being the microorganism on which the measures according to the invention are performed.

In order to achieve an attenuation, for example the expression of the genes or open reading frames, or the catalytic properties of the enzyme proteins, can be reduced or abolished. Where appropriate, both measures can be combined.

Gene expression can be reduced by carrying out the culture in a suitable manner, by genetically altering (mutating) the signal structures for the gene expression or by means of the antisense RNA technique. Signal structures for the gene expression are, for example, repressor genes, activator genes, operators, promoters, attenuators, ribosome binding sites, the start codon and terminators. The skilled person can find information in this regard in, inter alia and for example, Jensen and Hammer (Biotechnology and Bioengineering 58:191-195 (1998)), in Carrier and Keasling (Biotechnology Progress 15:58-64 (1999)), in Franch and Gerdes (Current Opinion in Microbiology 3:159-164 (2000)) and in well known textbooks of genetics and molecular biology such as the textbook by Knippers ("Molekulare Genetik [Molecular Genetics]", 6th edition, Georg Thieme Verlag, Stuttgart, Germany, 1995) or that by Winnacker ("Gene und Klone [Genes and Clones]", VCH Verlagsgesellschaft, Weinheim, Germany, 1990).

Mutations which lead to a change or reduction in the catalytic properties of enzyme proteins are known from the prior art. Examples which may be mentioned are the articles by Qiu and Goodman (Journal of Biological Chemistry 272:8611-8617 (1997)), Yano et al. (Proceedings of the National Academy of Sciences of the United States of America 95:5511-5515 (1998)) and Wente and Schachmann (Journal of Biological Chemistry 266: 20833-20839 (1991)). Summaries can be found in known textbooks of genetics and molecular biology, such as that by Hagemann ("Allgemeine Genetik [General Genetics]", Gustav Fischer Verlag, Stuttgart, 1986).

Mutations which come into consideration are transitions, transversions, insertions and deletions of at least one (1) base pair or nucleotide. Depending on the effect of the mutation-elicited amino acid substitution on the enzyme activity, reference is made to missense mutations or to nonsense mutations. A missense mutation leads to the replacement of a given amino acid in a protein with a different amino acid, with the amino acid replacement in particular being non-conservative.

This thereby impairs the functional ability or activity of the protein and reduces it down to a value of from 0 to 75%, 0 to 50%, 0 to 25%, 0 to 10% or 0 to 5%. A nonsense mutation leads to a stop codon in the coding region of the gene and thus to premature termination of the translation. Insertions or deletions of at least one base pair in a gene lead to frame shift mutations which in turn result in incorrect amino acids being incorporated or in the translation being prematurely terminated. If a stop codon is formed in the coding region as a consequence of the mutation, this then also leads to translation being terminated prematurely. Deletions of at least one (1) or more codons typically also lead to complete loss of the enzyme activity.

Directions for generating these mutations belong to the prior art and can be obtained from known textbooks of genetics and molecular biology such as the textbook by Knippers ("Molekulare Genetik [Molecular Genetics]", 6th edition, Georg Thieme Verlag, Stuttgart, Germany, 1995), that by Winnacker "Gene und Klone, [Genes and Clones]", VHC Verlagsgesellschaft, Weinheim, Germany, 1990) or that by Hagemann ("Allgemeine Genetik [General Genetics]", Gustav Fischer Verlag, Stuttgart, 1986).

Suitable mutations in the genes can be incorporated into suitable strains by means of gene or allele exchange. A customary method is the method, described by Hamilton et al. (Journal of Bacteriology 171:4617-4622 (1989)), of gene exchange using a conditionally replicating pSC101 derivative pMAK705. Other methods described in the prior art, such as that of Martinez-Morales et al. (Journal of Bacteriology 181: 7143-7148 (1999)) or that of Boyd et al. (Journal of Bacteriology 182:842-847 (2000)), can also be used. It is likewise possible to transfer mutations in the relevant genes, or mutations which effect the expression of the relevant genes or open reading frames, into different strains by means of conjugation or transduction.

Furthermore, for the purpose of producing L-amino acids, in particular L-threonine, it can be advantageous, in addition to enhancing the open reading frame ytfQ, to eliminate undesirable side-reactions (Nakayama: "Breeding of Amino Acid Producing Microorganisms", in: Overproduction of Microbial Products, Krumphanzl, Sikyta, Vanek (eds.), Academic Press, London, UK, 1982).

The performance of the isolated bacteria, or of the fermentation process using these bacteria, is improved, with regard to one or more of the parameters selected from the group consisting of the product concentration (product per volume), the product yield (product formed per carbon source consumed) and the product formation (product formed per volume and time), or else other process parameters and combinations thereof, by at least 0.5%, at least 1%, at least 1.5% or at least 2%, based on the nonrecombinant microorganism or parent strain, or the fermentation process using this microorganism or parent strain.

The microorganisms which are prepared in accordance with the invention can be cultured in a batch process, in a fed-batch process, in a repeated fed-batch process or in a continuous process (DE102004028859.3 or U.S. Pat. No. 5,763,230). Known culturing methods are summarized in the textbook by Chmiel (Bioprozesstechnik 1. Einführung in die Bioverfahrenstechnik [Bioprocess technology 1. Introduction to bioprocess technology] (Gustav Fischer Verlag, Stuttgart, 1991)) or in the textbook by Storhas (Bioreaktoren und periphere Einrichtungen [Bioreactors and peripheral installations] (Vieweg Verlag, Brunswick/Wiesbaden, 1994)).

The culture medium to be used must satisfy the demands of the given strains in an appropriate manner. The American Society for Bacteriology manual "Manual of Methods for General Bacteriology" (Washington D.C., USA, 1981) contains descriptions of media for culturing a variety of microorganisms. Sugars and carbohydrates, such as glucose, sucrose, lactose, fructose, maltose, molasses, starch and, where appropriate, cellulose, oils and fats, such as soybean oil, sunflower oil, peanut oil and coconut fat, fatty acids, such as palmitic acid, stearic acid and linoleic acid, alcohols, such as glycerol and ethanol, and organic acids, such as acetic acid, may be used as the carbon source. These substances may be used individually or as a mixture. For example, it is possible to use mixtures of glucose and fructose in a ratio of approx. 1:1, as described in EP 1 225 230.

Organic nitrogen-containing compounds, such as peptones, yeast extract, meat extract, malt extract, corn steep liquor, soybean flour and urea, or inorganic compounds, such as ammonium sulfate, ammonium chloride, ammonium phosphate, ammonium carbonate and ammonium nitrate, may be used as the nitrogen source. The nitrogen sources may be used individually or as a mixture.

Phosphoric acid, potassium dihydrogen phosphate or dipotassium hydrogen phosphate, or the corresponding sodium-containing salts, may be used as the phosphorus source. In addition, the culture medium must contain salts of metals, such as magnesium sulfate or iron sulfate, which are required for growth. Finally, essential growth promoters, such as amino acids and vitamins, may be used in addition to the abovementioned substances. Suitable precursors can also be added to the culture medium. Said ingredients may be added to the culture in the form of a one-off mixture or suitably fed in during the culture.

The fermentation is generally carried out at a pH of from 5.5 to 9.0, in particular of from 6.0 to 8.0. Basic compounds, such as sodium hydroxide, potassium hydroxide, ammonia or ammonia water, or acidic compounds, such as phosphoric acid or sulfuric acid, are used in a suitable manner for controlling the pH of the culture. Antifoamants, such as fatty acid polyglycol esters, can be used for controlling foaming. Suitable selectively acting substances, for example antibiotics, can be added to the medium in order to maintain the stability of plasmids. Oxygen or oxygen-containing gas mixtures, such as air, are passed into the culture in order to maintain aerobic conditions. The temperature of the culture is normally from 25° C. to 45° C. and preferably from 30° C. to 40° C. The action of the microorganisms results in the L-amino acid being accumulated in the culture broth. The culture is continued until a maximum of L-amino acids or L-threonine has been formed. This objective is normally reached within 10 to 160 hours.

The L-amino acids can be isolated, collected or concentrated from the culture broth, which has been taken off, and then purified, where appropriate. Ion exchange chromatography and crystallization are typical methods for purifying the L-amino acids. These methods result in L-amino acids which are to a large extent pure.

It is likewise possible to prepare a product from the culture broth (=fermentation broth), which has been taken off, by removing the biomass of the bacterium, which is present in the culture broth, completely (100%) or almost completely, i.e. more than or greater than (>) 90%, and to a large extent, i.e. to an extent of 30%-100%, preferably greater than or equal to ($\geq$) 50%, $\geq$70% or $\geq$90%, or else completely (100%), leaving the remaining constituents of the fermentation broth in the product.

Separation methods such as centrifugation, filtration, decantation or flocculation, or a combination thereof, are used for removing or separating off the biomass. The resulting broth is then inspissated or concentrated using known methods, for example using a rotary evaporator, a thin film evaporator or a falling film evaporator, by means of reverse osmosis or by means of nanofiltration, or a combination of these methods.

This concentrated broth is then worked-up into what is preferably a flowable, finely divided powder using the methods of freeze drying, spray drying or spray granulation, or using other methods. This flowable, finely divided powder can then in turn be converted into a coarse-grain, readily flowable, storable, and to a large extent dust-free, product using suitable compacting or granulating methods. A total of more than 90% of the water is removed in this connection, such that the water content in the product is less than 10%, less than 5% or less than 3%.

L-amino acids can be analyzed by means of anion exchange chromatography followed by derivatization with ninhydrin, as described in Spackman et al. (Analytical Chemistry 30: 1190-1206 (1958)), or by means of reversed phase HPLC, so as described in Lindroth et al. (Analytical Chemistry 51: 1167-1174 (1979)).

The process according to the invention can be used for fermentatively preparing L-amino acids, such as L-threonine, L-isoleucine, L-valine, L-methionine, L-homoserine, L-tryptophan and L-lysine, in particular L-threonine.

The present invention is explained in more detail below with the aid of implementation examples. Minimal (M9) and complete (LB) media used for *Escherichia coli* are described by J. H. Miller (A short course in bacterial genetics (1992), Cold Spring Harbor Laboratory Press). The isolation of plasmid DNA from *Escherichia coli*, and also all techniques for restricting, ligating and treating with Klenow phosphatase and alkali phosphatase, are carried out as described in Sambrook et al. (Molecular Cloning—A Laboratory Manual (1989) Cold Spring Harbor Laboratory Press). Unless otherwise indicated, *Escherichia coli* are transformed as described in Chung et al. (Proceedings of the National Academy of Sciences of the United States of America 86:2172-2175 (1989)). The incubation temperature when preparing strains and transformants is 37° C.

EXAMPLES

Example 1

Constructing the Expression Plasmid pMW218ytfQ

The *E. coli* K12 ytfQ gene is amplified using the polymerase chain reaction (PCR) and synthetic oligonucleotides. PCR primers are synthesized (MWG Biotech, Ebersberg, Deutschland) on the basis of the nucleotide sequence of the ytfQ gene in *E. coli* K12 MG1655 (Accession Number U00096 (Region: 4447895-4449841), Blattner et al. (Science 277:1453-1474 (1997)):

```
ytfQ-1: 5'-ACCGTAGCCGCATTTTTC-3'     (SEQ ID NO:5)

ytfQ-2: 5'-AATCGGCATCAGGCATAG-3'.    (SEQ ID No:6)
```

The *E. coli* K12 MG1655 chromosomal DNA used for PCR is isolated using "Qiagen Genomic-tips 100/G" (QIAGEN, Hilden, Germany) in accordance with the manufacturer's instructions. A DNA fragment of approx. 1152 bp in size (SEQ ID NO:7) can be amplified under standard PCR conditions (Innis et al. (1990) PCR Protocols. A Guide to Methods and Applications, Academic Press) using Vent DNA polymerase (New England Biolaps GmbH, Frankfurt, Germany) and the specific primers.

The amplified ytfQ fragment is ligated to the vector pCR-Blunt II-TOPO (Zero TOPO TA Cloning Kit, Invitrogen, Groningen, Netherlands) in accordance with the manufacturer's instructions and transformed into the *E. coli* strain TOP10. Plasmid-harboring cells are selected on LB Agar containing 50 µg of kanamycin/ml. After the plasmid DNA has been isolated, the vector is cleaved with the enzymes PvuI and EcoRI and, after the cleavage has been checked in a 0.8% agarose gel, designated pCRBluntytfQ.

The vector pCRBluntytfQ is then cleaved with the enzyme EcoRI and the ytfQ fragment is separated in a 0.8% agarose gel; it is then isolated from the gel (QIAquick Gel Extraction Kit, QIAGEN, Hilden, Germany) and ligated to the low-copy vector pMW218 (Nippon Gene, Toyama, Japan) which has been digested with the enzyme EcoRI. The *E. coli* strain DH5α (Grant et al.; Proceedings of the National Academy of Sciences USA 87:4645-4649 (1990)) is transformed with the ligation mixture and plasmid-harboring cells are selected on LB agar containing 50 µg of kanamycin/ml.

The fact that cloning has been successful can be demonstrated, after the plasmid DNA has been isolated, by performing a control cleavage using the enzyme PvuI. The plasmid is designated pMW218ytfQ (FIG. 1).

Example 2

Preparing L-threonine using the Strain MG442/pMW218ytfQ

The L-threonine-producing *E. coli* strain MG442 is described in the patent specification U.S. Pat. No. 4,278,765 and is deposited in the Russian national collection of industrial microorganisms (VKPM, Moscow, Russia) as CMIM B-1628.

The strain MG442 is transformed with the expression plasmid pMW218ytfQ described in example 1, and with the vector pMW218, and plasmid-harboring cells are selected on LB agar containing 50 µg of kanamycin/ml. This results in the strains MG442/pMW218ytfQ and MG442/pMW218. Selected individual colonies are then propagated further on minimal medium having the following composition: 3.5 g of $Na_2HPO_4*2H_2O$/l, 1.5 g of $KH_2PO_4$/l, 1 g of $NH_4Cl$/l, 0.1 g of $MgSO_4*7H_2O$/l, 2 g of glucose/l, 20 g of agar/l, 50 mg of kanamycin/l. The formation of L-threonine is checked in 10 ml batch cultures which are contained in 100 ml Erlenmeyer flasks. For this, a 10 ml preculture medium of the following composition: 2 g of yeast extract/l, 10 g of $(NH_4)_2SO_4$/l, 1 g of $KH_2PO_4$/l, 0.5 g of $MgSO_4*7H_2O$/l, 15 g of $CaCO_3$/l, 20 g of glucose/l, 50 mg of kanamycin/l, is inoculated and incubated, at 37° C. and 180 rpm for 16 hours, on a Kühner AG ESR incubator (Birsfelden, Switzerland). In each case 250 µl of this preliminary culture are inoculated over into 10 ml of production medium (25 g of $(NH_4)_2SO_4$/l, 2 g of $KH_2PO_4$/l, 1 g of $MgSO_4*7H_2O$/l, 0.03 g of $FeSO_4*7H_2O$/l, 0.018 g of $MnSO_4*1H_2O$/l, 30 g of $CaCO_3$/l, 20 g of glucose/l, 50 mg of kanamycin/l) and incubated at 37° C. for 48 hours. After the incubation, the optical density (OD) of the culture suspension is determined at a measurement wavelength of 660 nm using a Dr. Lange LP2W photometer (Düsseldorf, Germany).

An Eppendorf-BioTronik amino acid analyzer (Hamburg, Germany) is then used to determine, by means of ion exchange chromatography and post-column reaction involving ninhydrin detection, the concentration of the resulting L-threonine in the culture supernatant, which has been sterilized by filtration. The results of the experiment are shown in table 1.

TABLE 1

| Strain | OD (660 nm) | L-Threonine g/l |
|---|---|---|
| MG442/pMW218 | 6.4 | 2.15 |
| MG442/pMW218ytfQ | 5.5 | 2.6 |

All references cited herein are fully incorporated by reference. Having now fully described the invention, it will be understood by those of skill in the art that the invention may be practiced within a wide and equivalent range of conditions, parameters and the like, without affecting the spirit or scope of the invention or any embodiment thereof.

What is claimed is:

1. A recombinant or transformed microorganism comprising an enhanced or overexpressed ytfQ ORF nucleic acid encoding a ytfQ polypeptide having the amino acid sequence of either SEQ ID NO:2 or SEQ ID NO:4, wherein said ytfQ polypeptide is a binding protein of an ATP-dependent sugar transporter.

2. The recombinant or transformed microorganism of claim 1, wherein said ytfQ polypeptide consists of the amino acid sequence of either SEQ ID NO:2 or SEQ ID NO:4.

3. The recombinant or transformed microorganism of claim 1, wherein said nucleic acid comprises the nucleotide sequence of either SEQ ID NO:1 or SEQ ID NO:3.

4. The recombinant or transformed microorganism of claim 1, wherein said nucleic acid consists of the nucleotide sequence of either SEQ ID NO:1 or SEQ ID NO :3.

5. The recombinant or transformed microorganism of claim 1, wherein said nucleic acid is a polynucleotide sequence which hybridizes, under stringent conditions, to the sequence which is complementary to the sequence of SEQ ID NO: 1 or SEQ ID NO: 3, said stringent conditions comprising a washing step performed at a temperature of from 64° to 68° and at a salt concentration of the buffer of from 2×SSC to 0.1×SSC.

6. The recombinant or transformed microorganism of claim 1, wherein said recombinant or transformed microorganism belongs to a genus selected from the group consisting of: *Escherichia, Erwinia, Providencia* and *Serratia*.

7. The recombinant or transformed microorganism of claim 1, wherein said recombinant or transformed microorganism produces L-threonine.

8. The recombinant or transformed microorganism of claim 1 produced by transforming a microorganism with a vector comprising a nucleotide sequence encoding the ytfQ polypeptide of either SEQ ID NO:2 or SEQ ID NO:4, wherein said sequence is under the control of a promoter.

9. The recombinant or transformed microorganism of claim 8, wherein said nucleotide sequence is a polynucleotide sequence which hybridizes, under stringent conditions, to a sequence which is complementary to the sequence of SEQ ID NO:1 or SEQ ID NO:3, said stringent conditions comprising a washing step performed at a temperature of from 64° C to 68° C and at a salt concentration of the buffer of from 2×SSC to 0.1×SSC.

10. The recombinant or transformed microorganism of claim 8, wherein said recombinant or transformed microorganism belongs to a genus selected from the group consisting of: *Escherichia, Erwinia, Providencia* and *Serratia*.

11. A process for preparing a desired L-amino acid by fermentation comprising:
   a) culturing the recombinant or transformed microorganism of claim 1 in a medium under conditions under which the desired L-amino acid is accumulated in the medium or in the cells.

12. The process of claim 11, further comprising:
   b) after step a), isolating a composition comprising the desired L-amino acid.

13. The process of claim 11, wherein said recombinant or transformed microorganism comprises at least one additional gene that is enhanced relative to non-recombinant microorganisms of the same species, said additional gene being selected from the group consisting of:
   a) at least one gene of the thrABC operon encoding aspartate kinase, homoserine dehydrogenase, homoserine kinase and threonine synthase,
   b) the pyruvate carboxylase-encoding *Corynebacterium glutamicum* pyc gene,
   c) the phosphoenolpyruvate synthase-encoding pps gene,
   d) the phosphoenolpyruvate carboxylase-encoding ppc gene,
   e) the pntA and pntB genes encoding the subunits of pyridine transhydrogenase,
   f) the rhtC gene encoding the threonine resistance-mediating protein,
   g) the threonine export carrier protein-encoding *Corynebacterium glutamicum* thrE gene,
   h) the glutamate dehydrogenase-encoding gdhA gene,
   i) the ptsH gene encoding the phosphohistidine protein hexose phosphotransferase,
   j) the ptsI gene encoding enzyme I of the phosphotransferase system,
   k) the crr gene encoding the glucose-specific IIA component,
   l) the ptsG gene encoding the glucose-specific IIBC component,
   m) the cysteine synthase A-encoding cysK gene,
   n) the cysB gene encoding the regulator of the cys regulon,
   o) the cysJ gene encoding the NADPH sulfite reductase flavoprotein,
   p) the cysI gene encoding the NADPH sulfite reductase hemoprotein,
   q) the adenylyl sulfate reductase-encoding cysH gene,
   r) the sucA gene encoding the decarboxylase subunit of 2-ketoglutarate dehydrogenase,
   s) the sucB gene encoding the dihydrolipoyltrans-succinase E2 subunit of 2-ketoglutarate dehydrogenase,
   t) the sucC gene encoding the β-subunit of succinyl-CoA synthetase,
   u) the sucD gene encoding the α-subunit of succinyl-CoA synthetase,
   v) the gene product of the *Escherichia coli* yibD open reading frame (ORF),
   w) the gene product of the *Escherichia coli* yjcG open reading frame (ORF),
   x) the gene product of the *Escherichia coli* ytfR open reading frame (ORF),
   y) the gene product of the *Escherichia coli* ytfT open reading frame (ORF),
   z) the gene product of the *Escherichia coli* yjfF open reading frame (ORF).

14. The process of claim 11, wherein relative to non-recombinant microorganisms of the same species, said recombinant or transformed microorganism comprises at least a partially attenuated metabolic pathway reducing the formation of the desired L-amino acid.

15. The process of claim 11, wherein said recombinant or transformed microorganism comprises at least one gene that is attenuated relative to non-recombinant microorganisms of the same species, said gene being selected from the group consisting of:
   a) the threonine dehydrogenase-encoding tdh gene,
   b) the malate dehydrogenase-encoding mdh gene,
   c) the gene product of the *Escherichia coli* yjfA open reading frame (orf),
   d) the gene product of the *Escherichia coli* ytfP open reading frame (orf),
   e) the pckA gene encoding the phosphoenolpyruvate carboxykinase,
   f) the pyruvate oxidase-encoding poxB gene,
   g) the dgsA gene encoding the DgsA regulator of the phosphotransferase system,
   h) the rpoS gene encoding the sigma$^{38}$ factor, and,
   i) the aspartate ammonium lyase-encoding aspA gene.

16. The process of claim 11, wherein said desired L-amino acid selected from the group consisting of: L-asparagine, L-serine, L-glutamate, L-glycine, L-alanine, L-cysteine, L-valine, L-methionine, L-proline, L-isoleucine, L-leucine, L-tyrosine, L-phenylalanine, L-histidine, L-lysine, L-tryptophan, L-arginine and L-homoserine.

17. The process of claim 11, wherein said desired L-amino acid is selected from the group consisting of: L-isoleucine, L-valine, L-methionine, L-homoserine, L-tryptophan and L-lysine are prepared.

18. A recombinant or transformed microorganism of claim 1, comprising a ytfQ polypeptide having the amino acid sequence of either SEQ ID NO:2 or SEQ ID NO:4, wherein the concentration or activity of said ytfQ polypeptide is increased by at least 10% relative to non-recombinant microorganisms of the same species.

19. The recombinant or transformed microorganism of claim 18, wherein said recombinant or transformed microorganism produces L-threonine.

* * * * *